United States Patent [19]
Hamman

[11] Patent Number: 5,513,434
[45] Date of Patent: May 7, 1996

[54] ROTARY CUTTER FOR EXTERNAL FIXATION PINS

[75] Inventor: Gary T. Hamman, Warsaw, Ind.

[73] Assignee: Zimmer, Inc., Warsaw, Ind.

[21] Appl. No.: 311,984

[22] Filed: Sep. 26, 1994

[51] Int. Cl.⁶ .............................. B26D 3/16; A61B 17/84
[52] U.S. Cl. .................................. 30/101; 30/102; 82/73
[58] Field of Search ................................ 30/101, 102, 96, 30/97; 82/46, 70.1, 70.2, 73, 76

[56] References Cited

U.S. PATENT DOCUMENTS

| | | | |
|---|---|---|---|
| 4,467,682 | 8/1984 | Huggins | 82/73 |
| 5,103,699 | 4/1992 | Brown | 30/101 X |

*Primary Examiner*—Douglas D. Watts
*Attorney, Agent, or Firm*—Todd A. Dawson

[57] ABSTRACT

This invention provides for a pin cutter which forms an annular groove about the periphery of the pin. The cutter includes a cutting wheel that is rotated relative to the pin and is gradually tightened to force the cutting wheel into the pin and thereby widen the groove. The cutting action is similar to a pipe cutter used by plumbers to cut a length of copper tubing. The operator can continue tightening the cutting wheel against the pin until the pin is severed. A portion of the pin extends through the housing of the cutter. Since the pin is gradually cut, less force is required to sever the pin. Further, less force is released by the pin as it is severed. The severed and free portion of the pin is retained within the housing in a controlled manner.

5 Claims, 4 Drawing Sheets

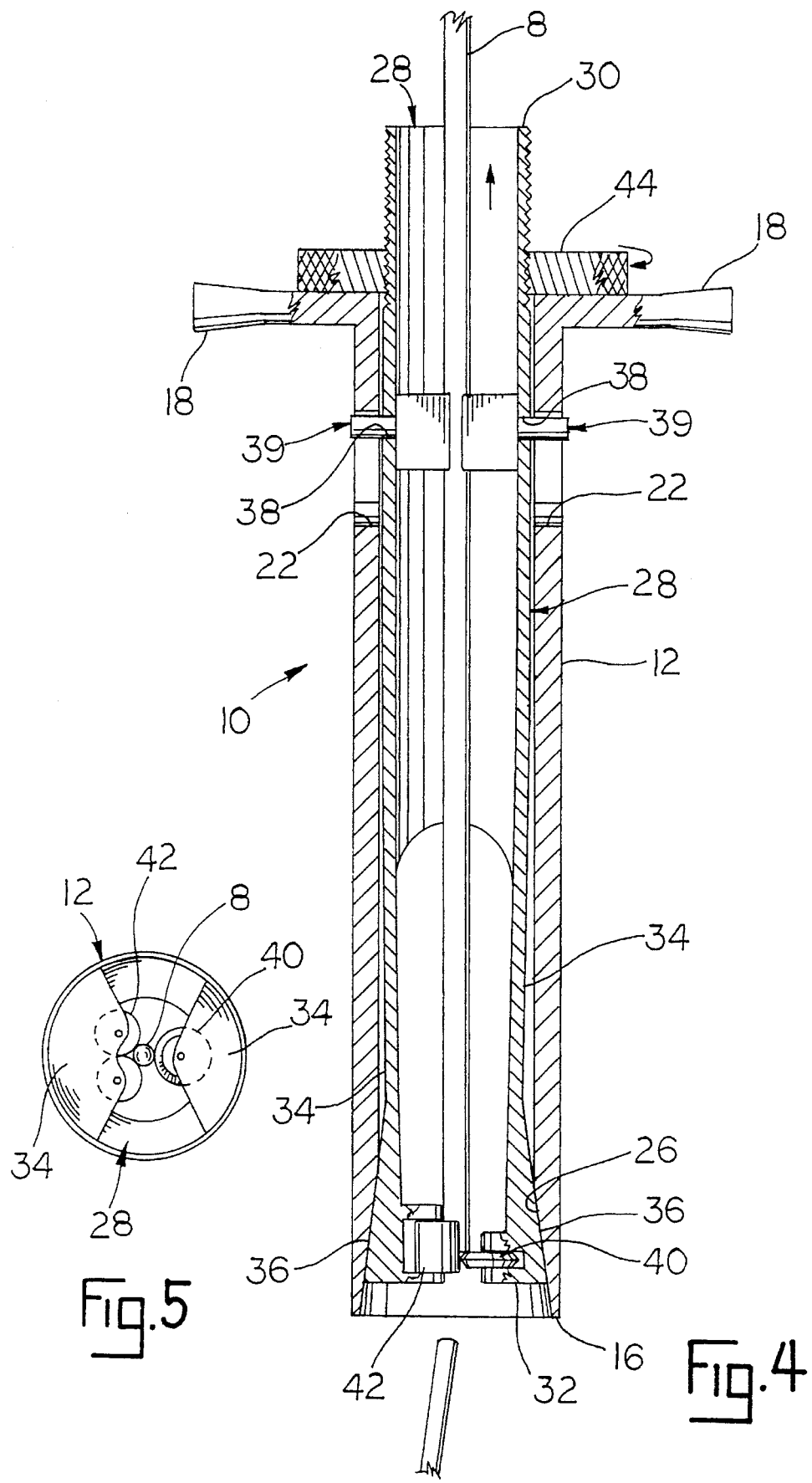

ROTARY CUTTER FOR EXTERNAL FIXATION PINS

FIELD OF THE INVENTION

This invention relates to cutting devices for cutting a pin adjacent an external fixator as used in orthopaedic fracture fixation and has specific relevance to a rotary pin cutter.

BACKGROUND OF THE INVENTION

To reduce a fracture of a long bone such as the tibia and maintain the bone fragments in a fixed relationship, a surgeon may choose to utilize an external fixator. External fixators are made by a number of orthopaedic instrument manufacturers. A common thread with the external fixators is that a pin or plurality of bone pins are inserted into the bone for connection to the fixator. The surgeon inserts a portion of the pin into the bone with the aid of a powered instrument. The remaining portion of the pin extends externally of the limb and is connected to the external fixation unit. Though the bone pins come in a variety of lengths, it is not uncommon for several inches of pin to extend beyond the fixator. For convenience, it is generally desirable to remove the excess portion of the pin. Currently, the pin is cut into by the use of a pair of large long handled scissors. Since the pins are stiff to prevent substantial bending and thereby ensure rigid fixation, when the pins are cut in this manner, a significant amount of energy is required. Further, when cut in this manner, the excised portion of the pin may become a projectile creating a dangerous situation. Lastly, a pin cut in this manner leaves a sharp end on the severed end which requires capping to prevent injury.

SUMMARY OF THE INVENTION

This invention provides for a pin cutter which forms an annular groove about the periphery of the pin. The cutter includes a cutting wheel that is rotated relative to the pin and is gradually tightened to force the cutting wheel into the pin and thereby widen the groove. The cutting action is similar to a pipe cutter used by plumbers to cut a length of copper tubing. The operator can continue tightening the cutting wheel against the pin until the pin is severed. A portion of the pin extends through the housing of the cutter. Since the pin is gradually cut, less force is required to sever the pin. Further, less force is released by the pin as it is severed. The severed and free portion of the pin is retained within the housing in a controlled manner. Alternatively, the cutter could be used simply to score the periphery of the pin with a deep groove. The pin could be easily broken into at the score line by the surgeon. In either event, the remaining portion of the pin is left with a substantially smoother end as compared with a scissor cut pin and would generally not require capping.

Accordingly, it is an object of the invention to provide for a novel cutter for orthopaedic pins.

Another object of the invention is to provide for a rotary pin cutter for orthopaedic pins which forms a groove about the periphery of the pin.

Another object of the invention is to provide for a rotary pin cutter for orthopaedic pins which includes a cutting wheel held in compressive engagement with the pin as the cutter rotates about the pin.

Still other objects of the invention will become apparent upon a reading of the following description taken with the accompanying drawings.

BRIEF DESCRIPTION OF THE DRAWINGS

FIG. 4 is a continuation of FIG. 3 illustrating the pin severed.

FIG. 5 is a elevational view taken along lines 5—5 of FIG. 3.

DESCRIPTION OF THE PREFERRED EMBODIMENT

The preferred embodiment herein described is not intended to be exhaustive or to limit the invention to the precise form disclosed. Rather, it is chosen and described to best explain the invention so that others skilled in the art might utilize its teachings.

Figure 2:
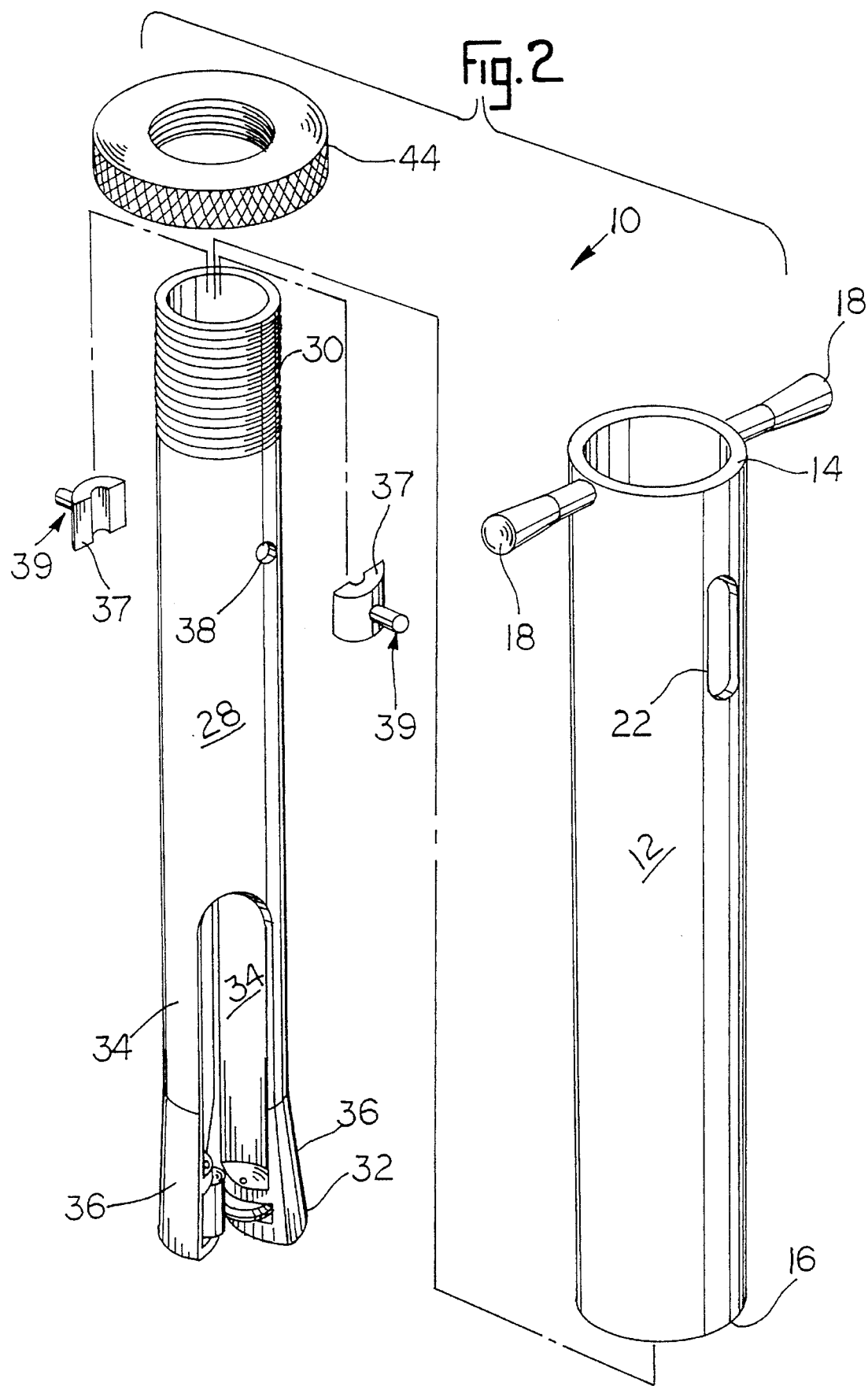
FIG. 2 is an exploded view of the cutter of FIG. 1 illustrating the components of the cutter.

Referring now to the drawings, rotary cutter 10 includes a generally tubular housing 12 having a proximal end 14 and a distal end 16. A pair of opposing handles 18 extend radially from the proximal end 14 of housing 12. A pair of slots 22 are formed through the side wall of housing 12. The distal end of the housing is internally chamfered to form a camming surface 26. As illustrated best in FIG. 2, cutter 10 includes an internal sleeve 28 having an externally threaded proximal end 30 and a distal end 32. Distal end 32 terminates in a pair of spaced legs 34. Each leg 34 includes an externally flared wall 36. Legs 34 may be biased from the normal position of FIG. 2 toward each other. Upon release of the biasing force, the legs will resume their normal position. Two through bores 38 are formed through sleeve 28 and accommodate the stems of insert guides 39 positioned within sleeve 28. Each insert guide includes an arcuate saddle portion 37 for accommodating surgical pin 8 between the two guides. A cutting wheel 40 is rotatably carried by one leg 34 generally transverse to the longitudinal dimension of sleeve 28 and extending toward the center of the sleeve. A pair of cylindrical rollers 42 are carried by the other leg 34 and are positioned so as to face cutting wheel 40. Rollers 42 are spaced slightly so as to form a seat therebetween for a surgical pin 8 as illustrated best in FIG. 5. Rollers 42 and cutting wheel 40 are carried adjacent the most distal end of sleeve 28.

Figure 1:
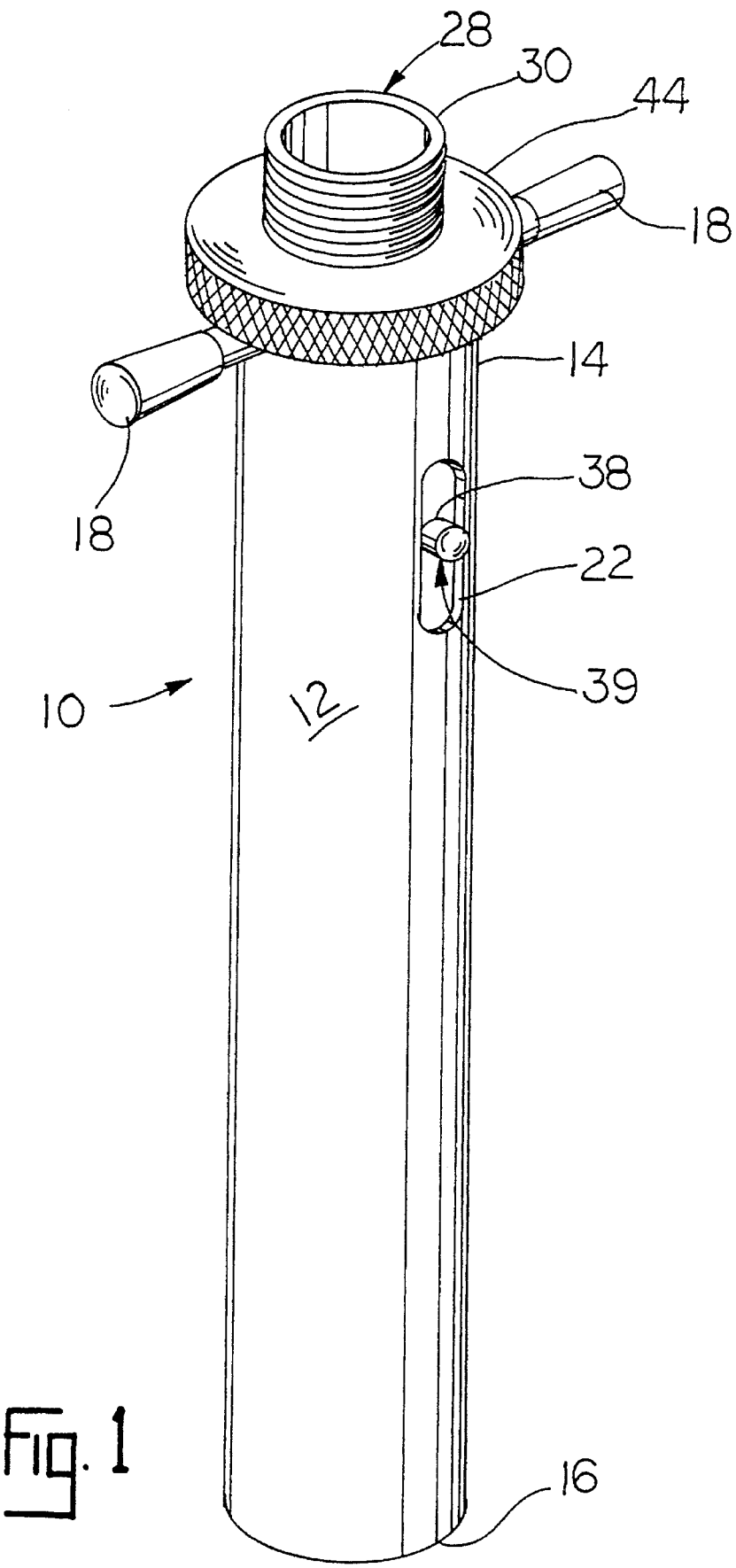
FIG. 1 is a perspective view of the rotary pin cutter of the invention.
Figure 3:
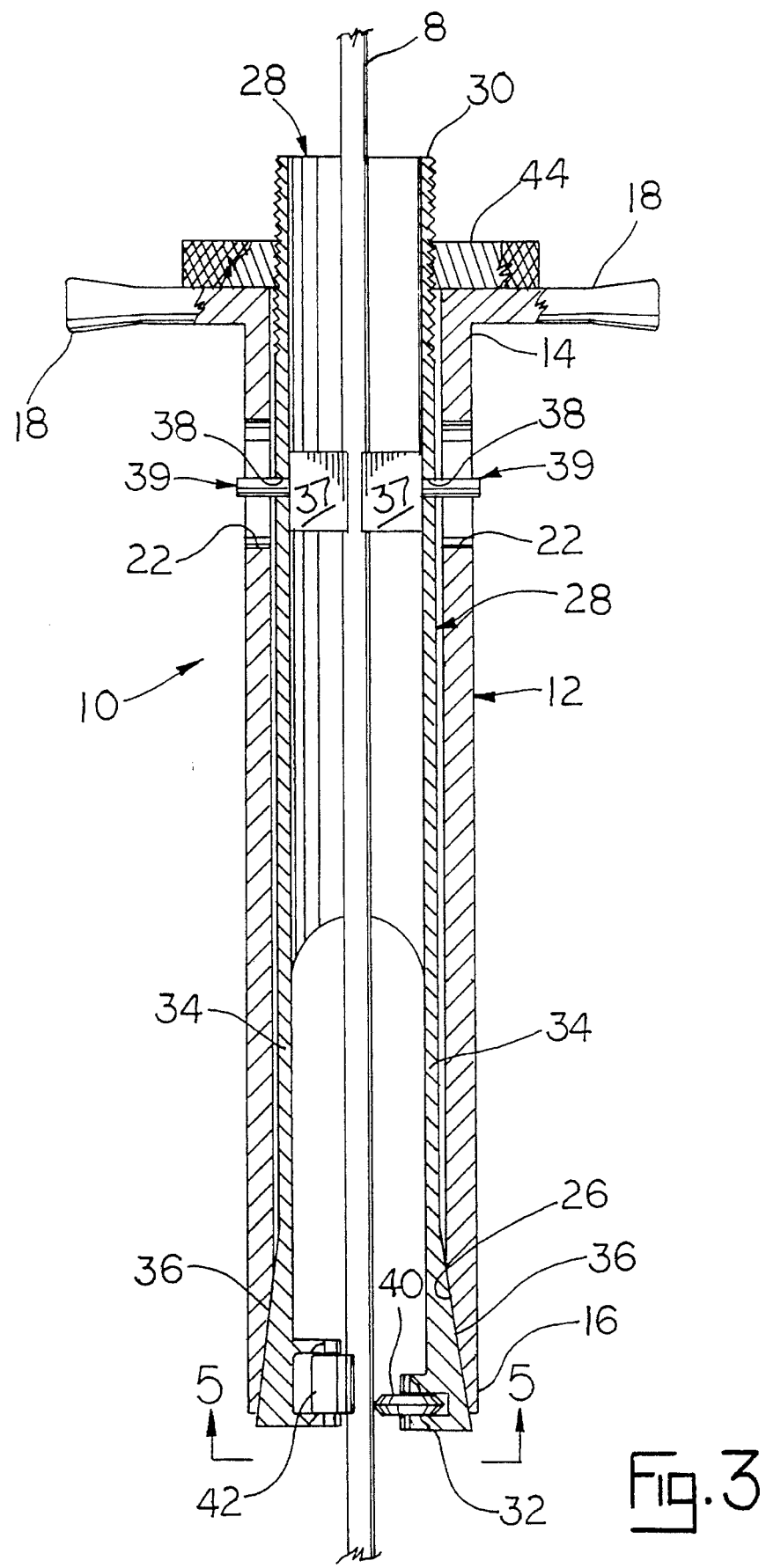
FIG. 3 is a side elevational view of the cutter of FIG. 1 placed over an orthopaedic pin with the cutting wheel in contact with the periphery of the surgical pin. Portions of the cutter have been sectioned for illustrative purposes.

In the assembled condition of FIGS. 1, 3, and 4, sleeve 28 is carried within housing 12 such that the threaded proximal end 30 of sleeve 28 extends beyond housing 12. A thumb wheel 44 is turned onto the external threads of sleeve 28. The stems of inserts 39 extend through openings 38 and are accommodated within the slots of the housing 12. To sever a pin 8, the rotary cutter is slid onto the pin with the distal end of the cutter being adjacent the fixator (not shown). As illustrated, the surgical pin is positioned between rollers 42 and cutting wheel 40 and is accommodated between the saddle portions 37 of inserts 39. To begin the cutting operation, thumb wheel 44 is turned further onto the proximal threaded end 30 of sleeve 28 thereby causing sleeve 28 to be drawn further into housing 12. As the sleeve is drawn into the housing, camming surface 26 of housing 12 contacts the outer bevelled walls 36 of legs 34 to bias the legs inwardly a small amount. As the legs are biased inwardly, the cutting wheel 40 pushes into the pin which is held against rollers 42. The user then rotates the cutter 10 using handles 18 and thereby rotates housing 12 and sleeve 28. The stems of inserts 39 extending through sleeve 28 and housing 12 rotationally fixes the housing and sleeve relative to each other. After the cutter 10 has been rotated about the pin a few revolutions, the cutting wheel 40 begins forming a groove (not shown) about the perimeter of the pin 8. The surgeon may again rotate thumb wheel 44 a few turns to continue to draw sleeve 28 further into the housing 12 thereby compressing cutting wheel 40 farther into pin 8. Again, the housing and sleeve are rotated and the cutting wheel deepens the groove in the periphery of the pin. The process continues until the cutting wheel completely severs the pin. Alternatively, the surgeon could form a deep groove in the pin to simply score the pin. If used as a pin scoring device, after the groove is formed, the cutting device 10 is removed and the surgeon may snap the pin into at the score line.

Since the pin is gradually severed or scored and then snapped into, the energy required is much less than the energy required from the surgeon to scissor cut the pin into. Therefore, when the pin is completely severed by the cutting device of the invention, the severed portion does not release significant lateral energy and will be substantially retained within the cutting device. Inserts 39 aid in retaining the pin by providing a slight clamping force against the pin and yet allowing cutter 10 to rotate in the manner required.

It should be understood that although the invention is described for use with an external fixation pin, such should not be considered a limitation. The cutter of the invention would work equally well with any other type of pin or rod used in orthopaedics such as a spinal rod.

It should be further understood that the invention is not to be limited to the precise form disclosed but may be modified within the scope of the appended claims.

I claim:

1. A device for severing a pin used in orthopaedics, the device including an elongated housing having a proximal end and a distal end and a sleeve having a proximal end and a distal end, the sleeve is carried within the housing such that the distal end of the sleeve is adjacent the distal end of the housing, cutting means carried by the sleeve adjacent the distal end of the sleeve, the cutting means being configured to form an annular groove in the periphery of the pin, the device further including a means for longitudinally shifting the sleeve relative to the housing, the housing and the sleeve being rotationally fixed together, the cutting means being biased toward the pin as the sleeve distal end is drawn into the distal end of the housing, the housing and sleeve and cutting means are rotatable about the pin to cause the cutting means to form an annular groove in the periphery of the pin, the shifting means includes screw threads formed on the proximal end of the sleeve and a thumb wheel threadably carried by the threads, the sleeve proximal end extending beyond the housing proximal end and the thumb wheel contacting the proximal end of the housing, wherein as said thumb wheel is rotated in one direction, the sleeve is longitudinally shifted relative to the housing such that the proximal end of the sleeve extends farther away from the proximal end of the housing and the distal end of the sleeve is drawn closer to the proximal end of the housing.

2. The device of claim 1 wherein the cutting means includes a cutting wheel carried generally transverse to a longitudinal dimension of the sleeve, and at least two rollers forming a seat therebetween for cradling the pin as the cutter is biased against the pin.

3. The device of claim 1 wherein as said housing and sleeve are rotated relative to the pin and the shifting means gradually shifts the sleeve relative to the housing, the cutting means forms a deepening groove in the periphery of the pin to thereby sever the pin at the groove.

4. A device for severing a pin used in orthopaedics, the device including an elongated housing having a proximal end and a distal end and a sleeve having a proximal end and a distal end, the sleeve is carried within the housing such that the distal end of the sleeve is adjacent the distal end of the housing, cutting means carried by the sleeve adjacent the distal end of the sleeve, the cutting means being configured to form an annular groove in the periphery of the pin, the device further including a means for longitudinally shifting the sleeve relative to the housing, the housing and the sleeve being rotationally fixed together, the cutting means being biased toward the pin as the sleeve distal end is drawn into the distal end of the housing, the housing and sleeve and cutting means are rotatable about the pin to cause the cutting means to form an annular groove in the periphery of the pin, wherein the distal end of the housing is flared internally to form a camming surface, the distal end of the sleeve forming a pair of facing legs having outwardly beveled external walls, wherein as the distal end of the sleeve is drawn into the distal end of the housing the camming surface of the housing contacts the outer beveled external walls of the legs to bias the legs inwardly toward one another.

5. A cutting device for severing a pin as used in orthopaedics, the cutting device including a generally tubular housing having a proximal end and a distal end, a generally tubular sleeve having a distal end and a proximal end, the sleeve is carried within the housing such that the distal end longitudinally extends beyond the distal end of the housing and the proximal end extends beyond the proximal end of the housing, the proximal end of the sleeve including an external helical thread, a thumb wheel is rotatably carried by the proximal end of the sleeve and engages the thread to travel along the sleeve, the sleeve and the housing being rotationally fixed and longitudinally shiftable such that as the thumb wheel travels along the thread in one direction, the distal end of the sleeve is drawn toward the distal end of the housing, the distal end of the housing is internally bevelled to form a camming surface, the distal end of the sleeve forming at least two legs, each leg including an outwardly beveled external wall, wherein as the sleeve distal end is drawn toward the distal end of the housing, the camming surface of the housing contacts the outwardly beveled walls of the legs to bias the legs inwardly toward each other, one of the sleeve legs carrying a rotatable cutting wheel positioned generally transverse to a longitudinal dimension of the sleeve, one of the sleeve legs carrying a pair of rollers facing the cutting wheel.

\* \* \* \* \*